(12) United States Patent
Michelena et al.

(10) Patent No.: US 11,806,518 B2
(45) Date of Patent: Nov. 7, 2023

(54) PASSIVE THRUST BEARING ANGLE

(71) Applicant: HeartWare, Inc., Miami Lakes, FL (US)

(72) Inventors: Christopher M. Michelena, Miami, FL (US); David A. Schafir, Miami Shores, FL (US); Fernando Casas, Miami Lakes, FL (US); Mustafa Ertan Taskin, Cooper City, FL (US)

(73) Assignee: HeartWare, Inc., Miami Lakes, FL (US)

( * ) Notice: Subject to any disclaimer, the term of this patent is extended or adjusted under 35 U.S.C. 154(b) by 411 days.

(21) Appl. No.: 16/952,613

(22) Filed: Nov. 19, 2020

(65) Prior Publication Data

US 2021/0213186 A1 Jul. 15, 2021

Related U.S. Application Data

(60) Provisional application No. 62/959,458, filed on Jan. 10, 2020.

(51) Int. Cl.
*A61M 60/824* (2021.01)
*F04D 7/00* (2006.01)
(Continued)

(52) U.S. Cl.
CPC ........ *A61M 60/824* (2021.01); *A61M 60/148* (2021.01); *A61M 60/419* (2021.01);
(Continued)

(58) Field of Classification Search
CPC .. A61M 2205/0266; A61M 2205/0294; A61M 2205/04; A61M 2205/3523; A61M 2205/8206; A61M 2205/825; A61M 60/148; A61M 60/178; A61M 60/242; A61M 60/419; A61M 60/422; A61M 60/806; A61M 60/808; A61M 60/824; A61M 60/871; F04D 29/026; F04D 29/041; F04D 29/0413; F04D 29/181; F04D 3/005; F04D 7/00; F05D 2260/70; F05D 2260/77; F05D 2270/807; F05D 2300/505; F16C 2202/36; F16C 2316/18; F16C 2360/00; F16C 27/08; F16C 41/008
See application file for complete search history.

(56) References Cited

U.S. PATENT DOCUMENTS 5,054,938 A * 10/1991 Ide ..................... F16F 15/0237
384/119
5,092,878 A 3/1992 Miyata
(Continued)

OTHER PUBLICATIONS

International Search Report and Written Opinion dated May 18, 2021, for corresponding International Application No. PCT/US2020/061779; International Filing Date: Nov. 23, 2020 consisting of 14-pages.

(Continued)

*Primary Examiner* — George Manuel
(74) *Attorney, Agent, or Firm* — Shumaker & Sieffert, P.A.

(57) ABSTRACT

An implantable blood pump includes a tube including an inner wall, and wherein during operation of the blood pump, the impeller rotates within the tube and a distance between the inner wall of the tube and the thrust bearing decreases as a speed of the impeller increases.

20 Claims, 6 Drawing Sheets

(51) Int. Cl.
  *F04D 29/18* (2006.01)
  *F04D 29/041* (2006.01)
  *F16C 27/08* (2006.01)
  *A61M 60/148* (2021.01)
  *A61M 60/419* (2021.01)

(52) U.S. Cl.
  CPC ............. *F04D 7/00* (2013.01); *F04D 29/041* (2013.01); *F04D 29/181* (2013.01); *F16C 27/08* (2013.01); *A61M 2205/0266* (2013.01); *A61M 2205/0294* (2013.01); *A61M 2205/04* (2013.01); *A61M 2205/3523* (2013.01); *A61M 2205/825* (2013.01); *A61M 2205/8206* (2013.01); *F16C 2360/00* (2013.01)

(56) References Cited

U.S. PATENT DOCUMENTS

| | | |
|---|---|---|
| 6,293,901 B1 | 9/2001 | Prem |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,419,609 B2 | 4/2013 | Shambaugh, Jr. et al. |
| 8,506,471 B2 | 8/2013 | Bourque |
| 8,512,013 B2 | 8/2013 | LaRose et al. |
| 9,217,442 B2 | 12/2015 | Wiessler et al. |
| 9,561,313 B2 | 2/2017 | Taskin |
| 9,907,891 B2 | 3/2018 | Wiessler et al. |
| 2009/0112312 A1 | 4/2009 | LaRose et al. |
| 2009/0234447 A1* | 9/2009 | LaRose ............... A61M 60/165 417/423.1 |
| 2013/0066139 A1 | 3/2013 | Wiessler et al. |
| 2014/0079557 A1* | 3/2014 | LaRose ................ A61M 60/81 416/223 R |
| 2015/0322940 A1 | 11/2015 | Horvath et al. |
| 2016/0045654 A1 | 2/2016 | Connor |
| 2016/0271309 A1 | 9/2016 | Throckmorton et al. |
| 2018/0200421 A1 | 7/2018 | Wiessler et al. |
| 2018/0303989 A1 | 10/2018 | Casas |
| 2018/0335037 A1 | 11/2018 | Shambaugh, Jr. et al. |
| 2019/0060543 A1 | 2/2019 | Khanal et al. |
| 2019/0070345 A1 | 3/2019 | McBride et al. |
| 2021/0113751 A1 | 4/2021 | Casas et al. |

OTHER PUBLICATIONS

Scudellari, "A Fitbit for the Stomach > The ingestible, self-powered device tracks food ingestion," IEEE Spectrum, Oct. 11, 2017, 5 pp.
E.I. Radzimovsky, Lubrication of Bearings, Published by the Ronald Press Company, New York.
Fields, Sarah, It's a Bird, It's a Plane: Flow Patterns Around an Oscillating Piezoelectric Fan Blade, IEEE Spectrum, Oct. 2017 Publication.

* cited by examiner

PASSIVE THRUST BEARING ANGLE

CROSS-REFERENCE TO RELATED APPLICATION

This application claims the benefit of U.S. Application Ser. No. 62/959,458, filed Jan. 10, 2020.

FIELD

The present technology is generally related to smart pump impellers and passive thrust bearings.

BACKGROUND

Implantable blood pumps are commonly used to assist the pumping action of a failing heart and typically include a housing with an inlet, an outlet, and a rotor mounted therein. The inlet may be connected to a chamber of the patient's heart, typically the left ventricle, using an inflow cannula. The outlet may be connected to an artery, such as the aorta. Rotation of the rotor drives blood from the inlet towards the outlet and thus assists blood flow from the chamber of the heart into the artery. A known type of blood pump is a ventricular assist device ("VAD") with examples including, but not limited to, the HVAD® pump and the MVAD® pump manufactured by HeartWare, Inc. in Miami Lakes, Fla., USA.

Impellers for axial flow blood pumps include a plurality of blades radially disposed about a central hub with a plurality of thrust bearings disposed on the surface of the blades. These thrust bearings, which are hydrodynamic, bear the load imparted by the blood and the spinning impeller. However, current thrust bearings are static, in that they are disposed at a single angle and therefore operate at maximum efficiency at a single pump speed.

SUMMARY

The techniques of this disclosure generally relate to smart pump impellers and passive thrust bearings.

In one aspect, an impeller for an implantable blood pump includes at least one deformable thrust bearing disposed on a surface of the impeller.

In another aspect of this embodiment, the thrust bearing includes nitinol.

In another aspect of this embodiment, wherein the deformable thrust bearing defines a pocket depth, and wherein the implantable blood pump includes a tube including an inner wall, and wherein during operation of the blood pump, the impeller rotates within the tube the pocket depth decreases as a speed of the impeller increases.

In another aspect of this embodiment, the pocket depth increases as the speed of the impeller decreases.

In another aspect of this embodiment, the thrust bearing defines a thrust bearing angle with the surface of the impeller, and wherein the thrust bearing angle decreases as speed increases.

In another aspect of this embodiment, the thrust bearing angle increases as speed decreases.

In another aspect of this embodiment, the thrust bearing is a spring.

In another aspect of this embodiment, the thrust bearing includes a piezoelectric material.

In another aspect of this embodiment, the thrust bearing flexes in response to centrifugal forces imparted on the thrust bearing.

In one embodiment, an impeller for an implantable blood pump includes a hub defining a plurality of blades radially disposed about the hub. An electronics module is disposed within the hub, the electronics module including a kinematic energy harvesting system to convert rotational energy of the impeller during operation into electrical energy.

In another aspect of this embodiment, the electronics module includes a wireless transmitter and receiver.

In another aspect of this embodiment, the electronics module includes at least one from a group consisting of a capacitor and a battery.

In another aspect of this embodiment, the impeller further includes a plurality of drive magnets disposed within the housing.

In another aspect of this embodiment, the impeller further includes a thrust bearing, and wherein the thrust bearing includes a piezoelectric element configured to deform in response to an applied electric potential.

In another aspect of this embodiment, the kinematic harvesting element is in communication with the thrust bearing.

In another aspect of this embodiment, the electronics module includes an accelerometer.

In another aspect of this embodiment, the hub is hollow.

In another aspect of this embodiment, the hub is sized and configured to be received within a tube.

In another aspect of this embodiment, the implantable blood pump is an axial flow blood pump.

In one embodiment, an impeller for an implantable blood pump includes at least one deformable thrust bearing disposed on a surface of the impeller, the impeller including a plurality of blades disposed on the surface, the thrust bearing flexes in response to centrifugal forces imparted on the thrust bearing during operating of the implantable blood pump, the implantable blood pump includes a tube including an inner wall, the thrust bearing defines a pocket depth, and during operation of the blood pump, the impeller rotates within the tube and the pocket depth decreases as a speed of the impeller increases.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
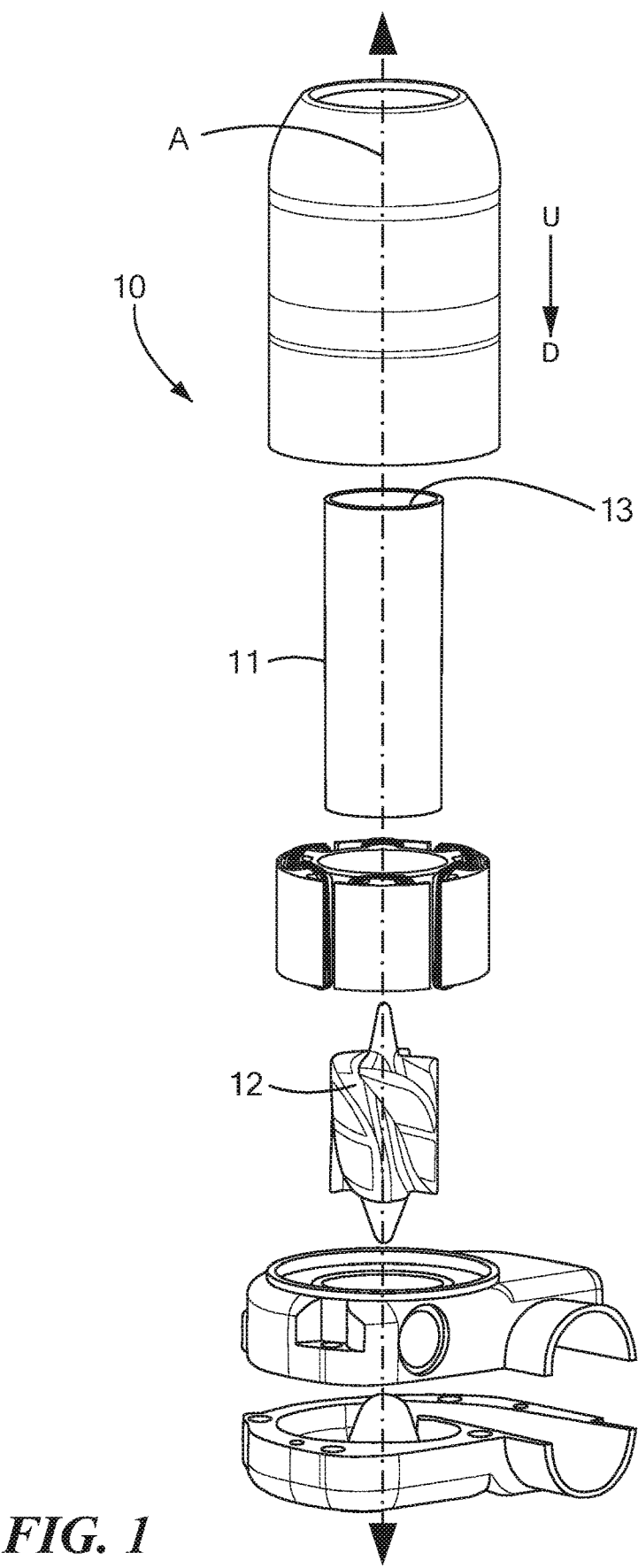
FIG. 1 is a disassembled view of an implantable blood pump.

Before describing in detail exemplary embodiments, it is noted that the configurations reside primarily in combinations of device and system components and method steps related to preventing or clearing an adverse event associated with an implantable blood pump. Accordingly, the device, system, and method components have been represented where appropriate by conventional symbols in the drawings, showing only those specific details that are pertinent to understanding the configurations of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate, and modifications and variations are possible of achieving the electrical and data communication.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

Referring now to the drawings in which like reference designators refer to like elements there is shown in FIG. 1 a disassembled view of an exemplary implantable blood pump 10 configured to be implanted within a patient, such as a human or animal patient. The blood pump 10 may be, without limitation, the HVAD® pump or the MVAD® pump, having a movable element, such as an impeller 12 or a rotor, configured to rotate about axis "A" and impel blood from the heart to the rest of the body. The impeller 12 may rotate within a tube 11 extending from a proximal upstream end to a distal downstream end. The HVAD® Pump is further discussed in U.S. Pat. Nos. 7,997,854 and 8,512,013, the disclosures of which are incorporated herein by reference in the entirety. The MVAD® Pump is further discussed in U.S. Pat. Nos. 8,007,254, 8,419,609, and 9,561,313, the disclosures of which are incorporated herein by reference in the entirety.

Figure 2:
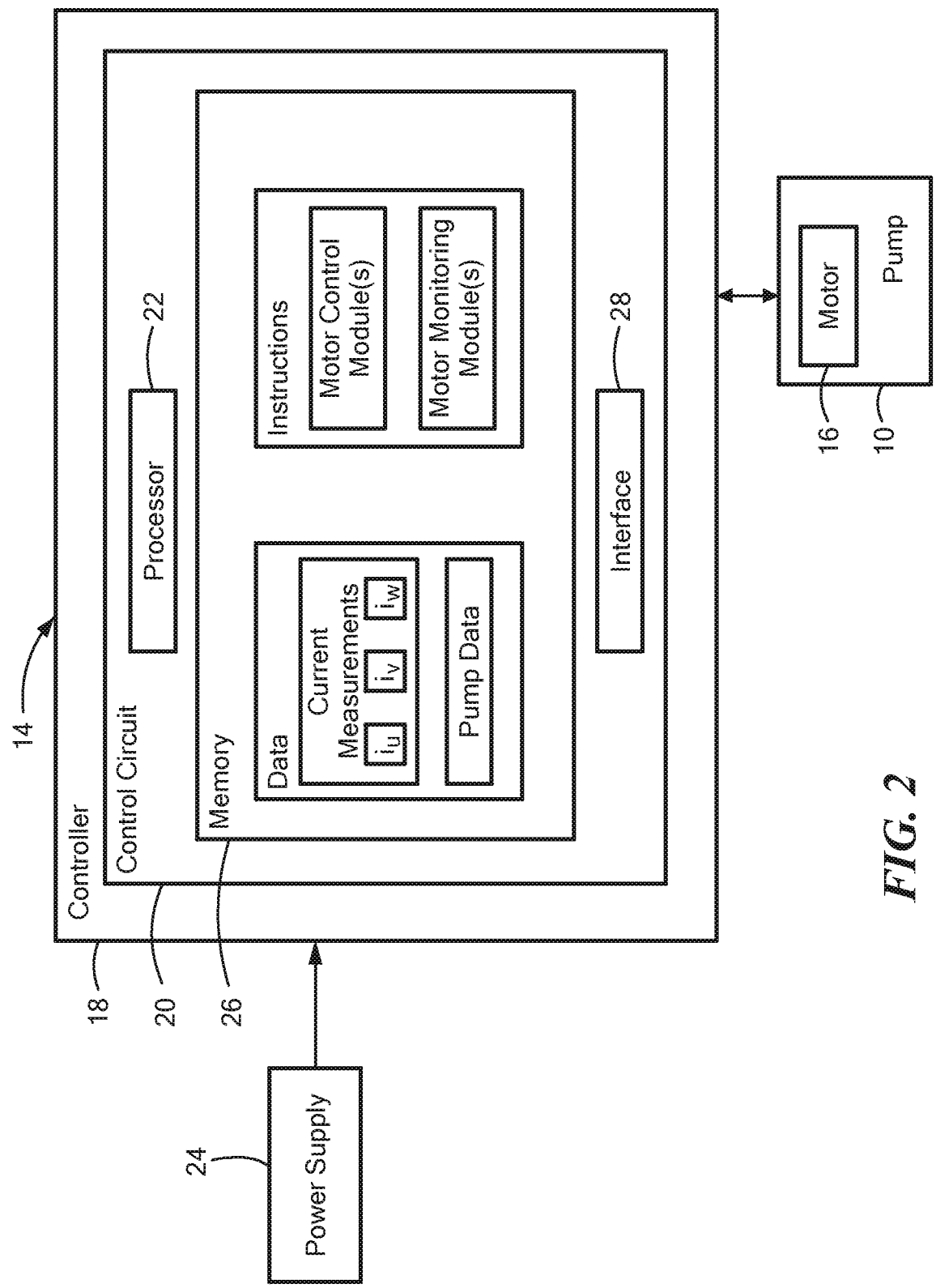
FIG. 2 is a block diagram of a system for controlling a pump speed of the blood pump of FIG. 1.

FIG. 2 is a block diagram of an exemplary system 14 for controlling a pump speed and/or other operations of the implantable blood pump 10 when the blood pump 10 is in communication with the system 14 and powered by a power supply 24. The blood pump 10 includes a motor 16 therein and may be a separate component or form part of the system 14. In one example, the system 14 includes a controller 18 having a control circuit 20 and a processor 22 including processing circuitry configured to perform the operations of the blood pump 10. The system 14 may also include a memory 26 and an interface 28, the memory 26 being configured to store information accessible by the processor 22, including instructions executable by the processing circuitry and/or data that may be retrieved, manipulated or stored by the processor 22. Such instructions and/or data include that which is used to control the pump speed.

Figure 3:
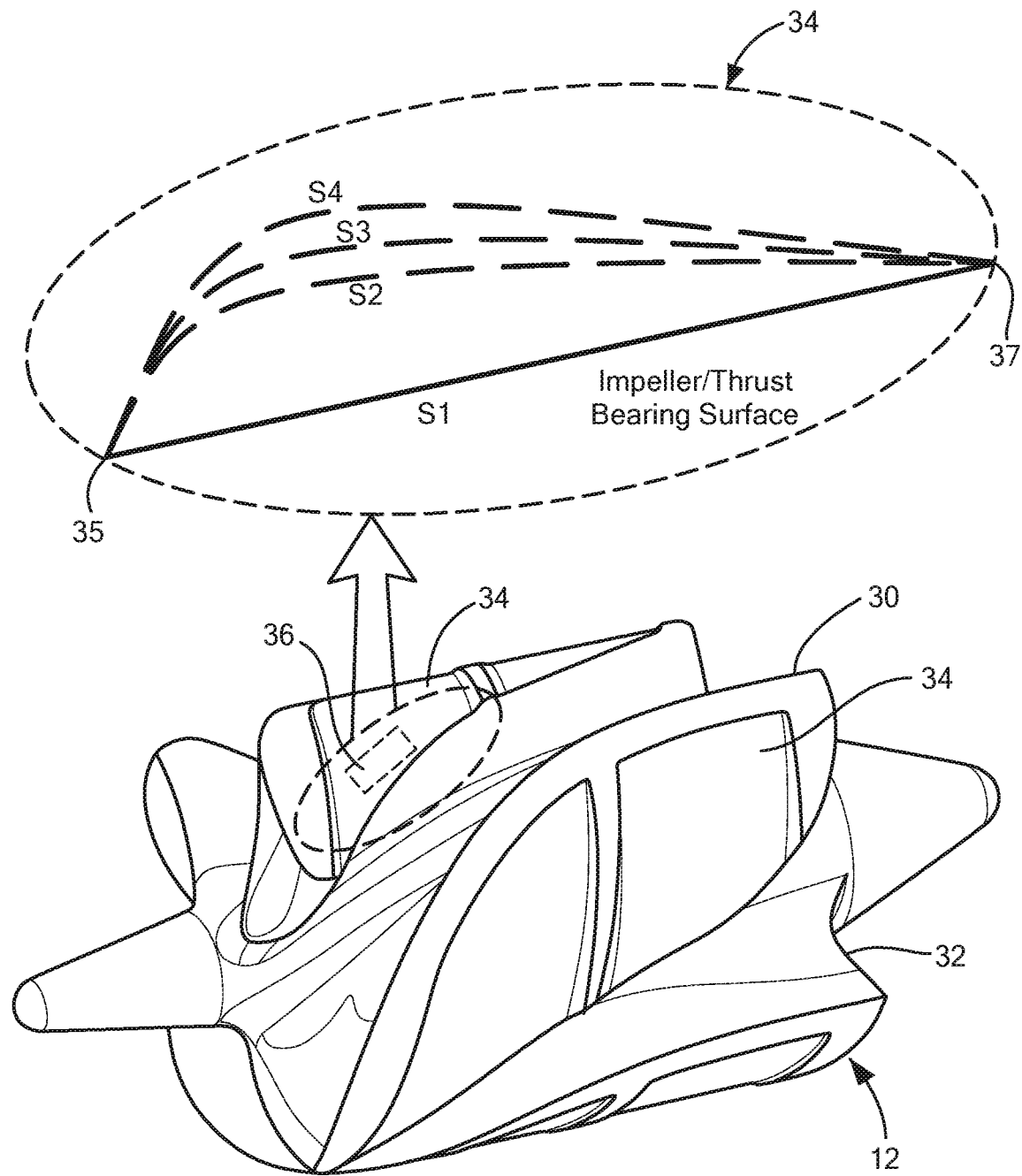
FIG. 3 is a perspective view of the impeller shown in FIG. 1 with a zoomed in view of a thrust bearing of the impeller constructed in accordance with the principles of the present application.
Figure 4:
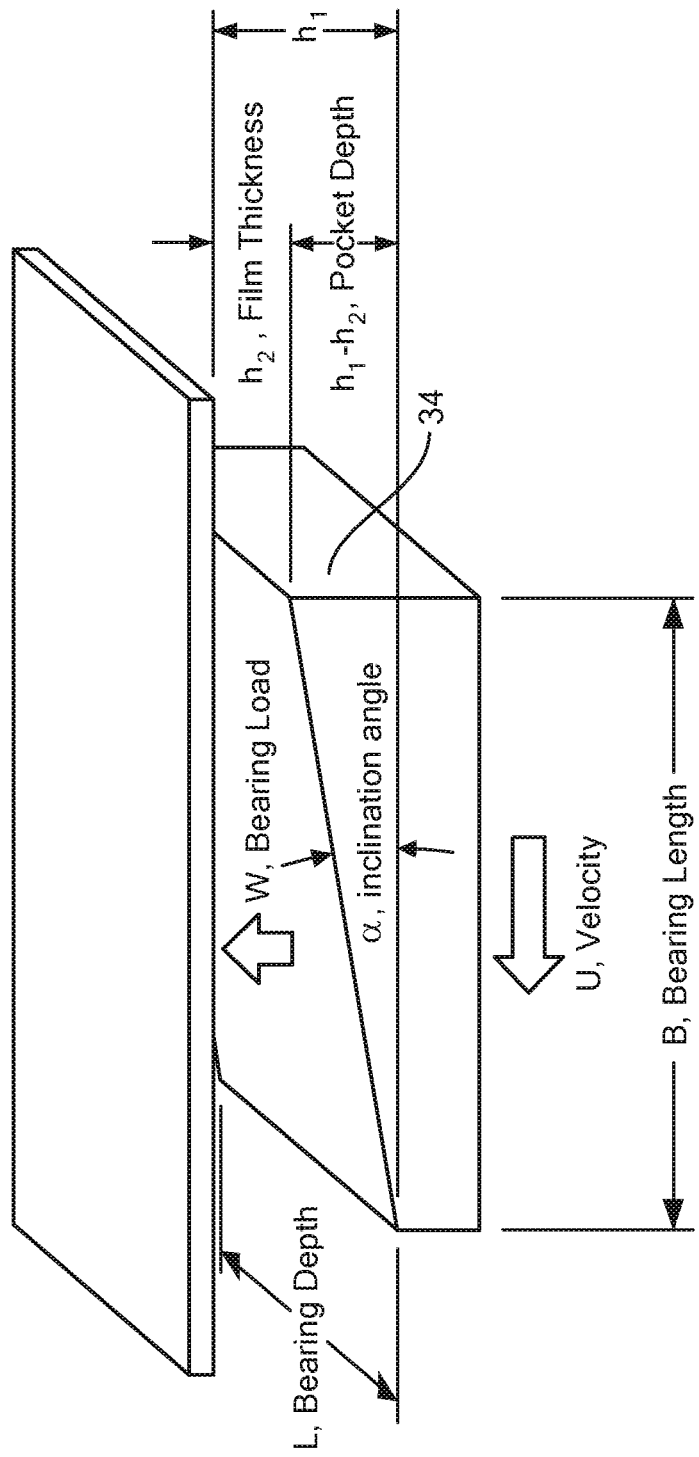
FIG. 4 is a schematic of the components of an exemplary thrust bearing shown constructed in accordance with the principles of the present application.
Figure 5:
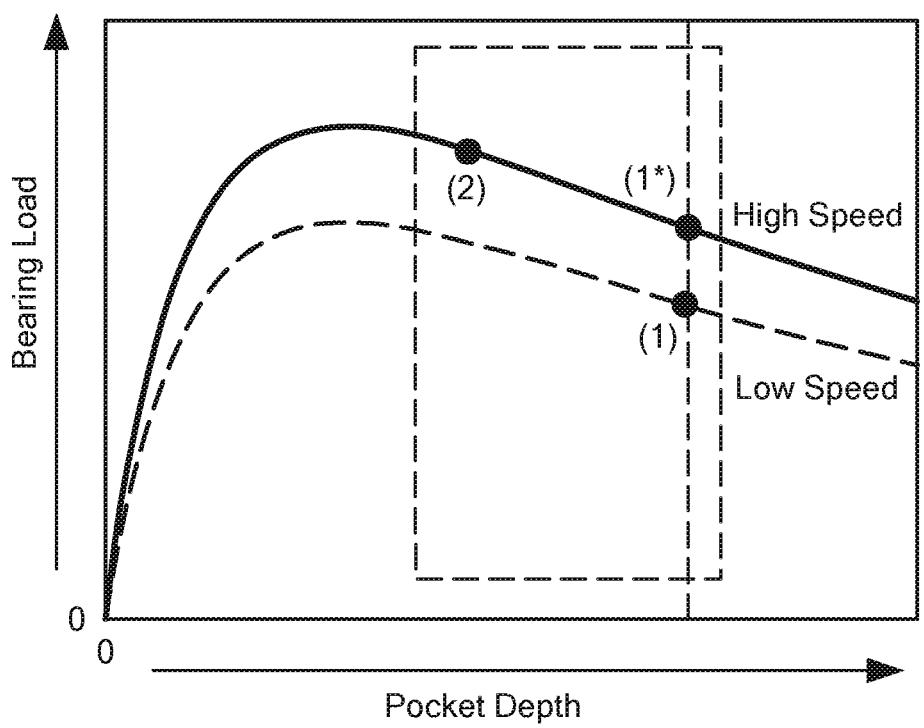
FIG. 5 is a graph showing bearing load as a function of pocket depth of an exemplary thrust bearing constructed in accordance with the principles of the present application.

Referring now to FIGS. 3-5, the impeller 12 may include a plurality of blades 30 radially disclose about a hub or body 32 of the impeller 12. Disposed on a surface of the blades 30 is at least one deformable thrust bearing 34 configured to bear the load imparted by the blood as the impeller 12 rotates within tube 11. The thrust bearing 34 may be composed of a deformable material, such as nitinol or other shape memory materials, such that owing to centrifugal forces, during operation of the blood pump 10 the impeller 12 rotates within the tube 11 and the thrust bearing deforms and a pocket depth ($h_1$-$h_2$) of the thrust bearing 34 decreases as a speed of the impeller 12 increases. Similarly, owing to centrifugal forces, the pocket depth ($h_1$-$h_2$) increases as the speed of the impeller 12 decreases, which decreases the load on the thrust bearing 34. In particular, load on a thrust bearing is governed by the following equation:

$$W = 6\mu L U \frac{1}{\alpha^2}\left[\ln\frac{a-\alpha}{a} + \frac{2\alpha}{2a-\alpha}\right] \text{ where } a = \frac{h^2}{B}$$

W is the bearing load, a is the bearing inclination angle, $h^2$ is the film thickness, L is the bearing depth, U is the velocity of the pump, and B is the bearing width. As the inclination angle α increases the bearing load W decreases, and vice versa. As the speed increases the inclination angle decreases. The increase in bearing load, W, as the speed increases on the thrust bearing 34 provides for a more stable bearing. Moreover, because movement of the thrust bearing 34 is caused by centrifugal forces on the thrust bearing 34, the thrust bearing 34 passively deforms in response to speed changes without the need for additional components to act on the thrust bearing 34. In particular, the thrust bearing 34 may be a spring, for example, a leaf spring that passively moves as the impeller 12 changes speed.

Figure 3A:
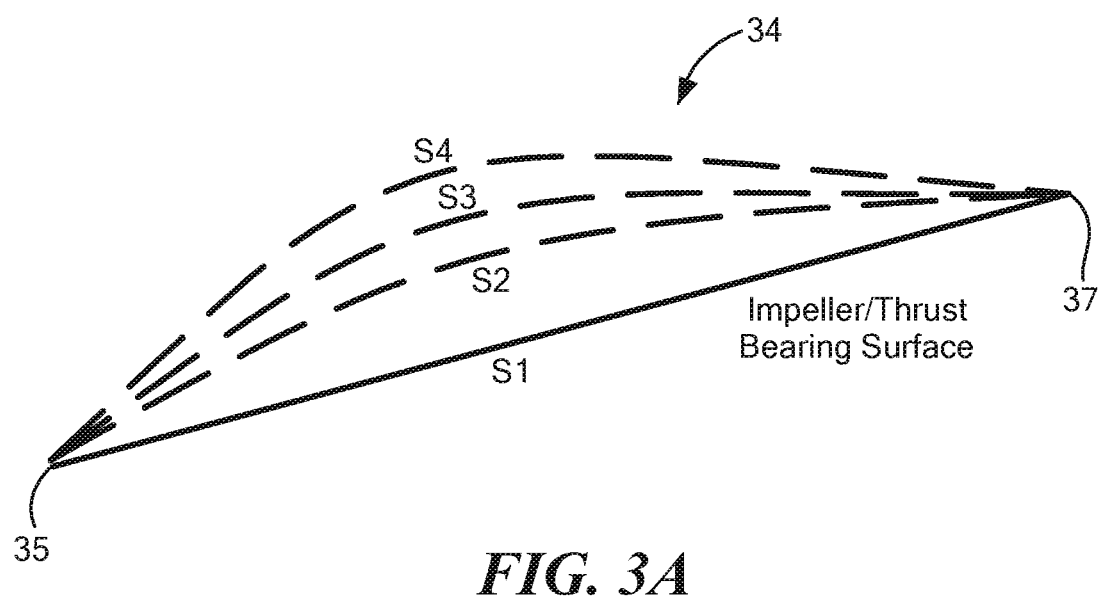
FIG. 3A is a zoomed in view of an alternative thrust bearing of the impeller constructed in accordance with the principles of the present application.

In one configuration, a first end 35 of the thrust bearing 34 may be coupled to a portion of the blades 30 and a second end 37 may be coupled to a different portion of the blades 30. As the speed of the impeller 12 increases from S1 to S4 the centrifugal forces acting on the thrust bearing increase which causes a bowing effect as the thrust bearing 34 deforms. In one configuration, as shown in FIG. 3, the thrust bearing 34 increasingly deforms outward proximate the first end 35 depending on the coupling between the first end 35, the second end 37, and the blades 39. In other configurations, as shown in FIG. 3A. the thrust bearing 34 deforms evenly between the first end 35 and the second end 37. In yet another configuration, the thrust bearing 34 deforms proximate the second end 37.

FIG. 5 shows speed differences and their effects on bearing load and pocket depth. Point (1) is a hypothetical point along an exemplary speed curve and point (1*) is a point based off (1) due to a higher speed with a static thrust bearing showing a higher bearing load, shown by the dotted line between points (1) and (1*). Point (2) is also based off of point (1) but due to a higher speed. The deformable thrust bearing 34 of the present disclosure decreases the pocket depth due to the centrifugal forces acting on the thrust bearing material and thus by creating a smaller pocket depth the bearing load increases from point (1*) to point (2).

Figure 6:
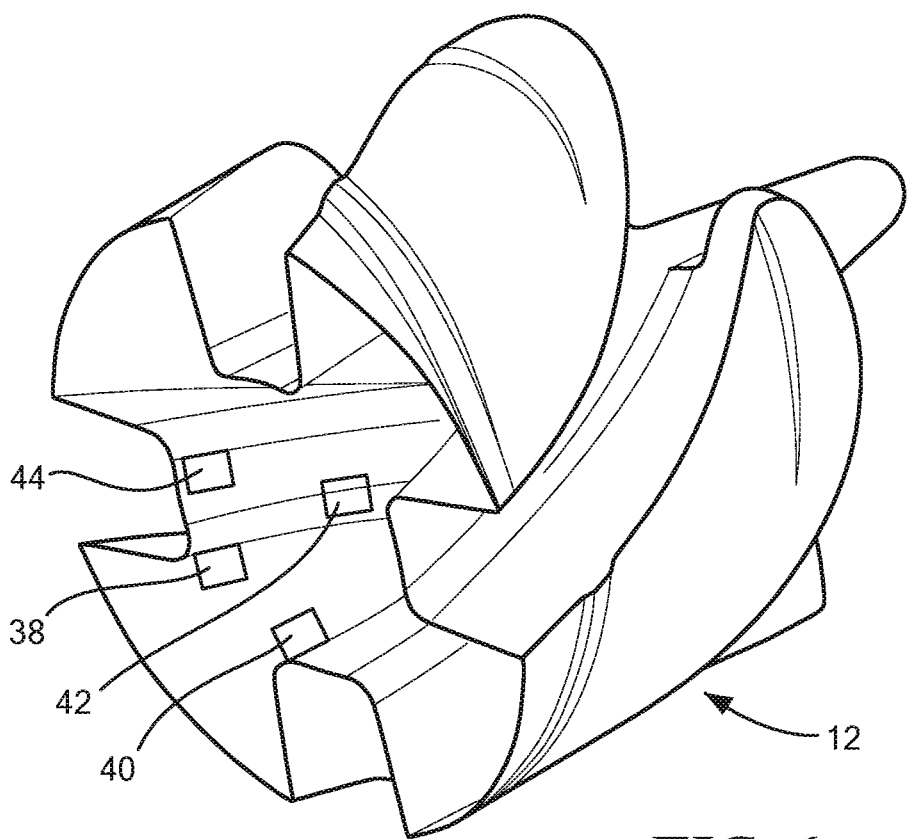
FIG. 6 is a perspective inside view of an impeller with electronic components disposed within and constructed in accordance with the principles of the present application.

In another configuration, the thrust bearing 34 optionally includes a piezoelectric element 36 configured to deform in response to an applied electric field. For example, the piezoelectric element 36 may be embedded or encased within the deformable thrust bearing 34 to isolate it from the blood flow. The piezoelectric element 36 may be in communication with a power source 38, which may be included within the hub 32 of the impeller 12. For example, as shown in FIG. 6, the hub 32 may be hollow and may be clam shell in design such that an interior of the hub 32 may be accessible to house the drive magnets that cause the impeller 12 to rotate and an electronics module 38 which may house various sensors and power sources away from the flowing blood. For example, the electronics module 38 may include a kinematic energy harvesting system 40 configured to convert the impeller's 12 kinetic energy into electrical energy that can be stored in a one or more batteries or capacitors. The battery or capacitor may be in communication with the piezoelectric element 36 to cause the piezoelectric element 36 to deform the thrust bearing 34 at predetermined times or intervals. The electronics module 38 may include processing circuitry configured to intermittently apply an electric potential to the piezoelectric element 36, which may cause a pulsatile effect on the pump 10, which may wash or rinse the impeller 12 and mitigate thrombus. In addition to the kinematic energy harvesting system 40, the electronics module 38 may include a telemetry system 42, including a transmitter and a receiver to communicate with an external controller (not shown), and an accelerometer 44 to providing information about the impeller 12's position and movement. The accelerometer 44 may communicate with the processing circuitry of the of the electronics module 38 to time the application of the electric potential to the piezoelectric material 36.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An impeller for an implantable blood pump, comprising:
    at least one deformable thrust bearing disposed on a surface of a body of the impeller, wherein the deformable thrust bearing is configured to experience centrifugal forces when the body of the impellor rotates, and
    wherein the deformable thrust bearing is configured to deform outward relative to the surface when the deformable thrust bearing experiences the centrifugal forces.

2. The impeller of claim 1, wherein the thrust bearing includes nitinol.

3. The impeller of claim 1, wherein the deformable thrust bearing defines a pocket depth, wherein the implantable blood pump includes a tube including an inner wall, wherein the impeller is configured to rotate within the tube, and wherein the deformable thrust bearing is configured to decrease the pocket depth as a speed of the impeller increases.

4. The impeller of claim 1, wherein the deformable thrust bearing defines a pocket depth, wherein the implantable blood pump includes a tube including an inner wall, wherein the impeller is configured to rotate within the tube, and wherein the deformable thrust bearing is configured to increase the pocket depth as a speed of the impeller decreases.

5. The impeller of claim 1, wherein the deformable thrust bearing defines a thrust bearing angle with the surface of the impeller, and wherein the deformable thrust bearing is configured to decrease the thrust bearing angle as a speed of the impeller increases.

6. The impeller of claim 1, wherein the deformable thrust bearing defines a thrust bearing angle with the surface of the impeller, and wherein the deformable thrust bearing is configured to increase the thrust bearing angle as a speed of the impeller decreases.

7. The impeller of claim 1, wherein the thrust bearing is a spring.

8. The impeller of claim 1, wherein the thrust bearing includes a piezoelectric material.

9. The impeller of claim 1, wherein the thrust bearing is configured to flex in response to the centrifugal forces imparted on the thrust bearing.

10. An impeller for an implantable blood pump, comprising:
    a hub defining a plurality of blades radially disposed about the hub;
    an electronics module disposed within the hub, the electronics module including a kinematic energy harvesting system to convert rotational energy of the impeller during operation into electrical energy.

11. The impeller of claim 10, wherein the electronics module includes a wireless transmitter and receiver.

12. The impeller of claim 11, wherein the electronics module includes at least one of a capacitor or a battery.

13. The impeller of claim 10, further including a plurality of drive magnets disposed within the hub.

14. The impeller of claim 10, further including a thrust bearing, wherein the thrust bearing includes a piezoelectric element configured to deform in response to an applied electric potential.

15. The impeller of claim 14, wherein the kinematic energy harvesting system is configured to communicate with the thrust bearing.

16. The impeller of claim 10, wherein the electronics module includes an accelerometer.

17. The impeller of claim 10, wherein the hub is hollow.

18. The impeller of claim 10, wherein the hub is sized and configured to be received within a tube.

19. The impeller of claim 18, wherein the implantable blood pump is an axial flow blood pump.

20. An impeller for an implantable blood pump, comprising:

at least one deformable thrust bearing disposed on a surface of a body of the impeller, the impeller including a plurality of blades disposed about the body, wherein the implantable blood pump includes a tube including an inner wall, wherein the impeller is configured to rotate within the tube, wherein the deformable thrust bearing is configured to deform outward relative to the surface when the impellor rotates within the tube and the deformable thrust bearing experiences centrifugal forces, wherein the thrust bearing defines a pocket depth, wherein the deformable thrust bearing is configured to decrease the pocket depth as a speed of the impeller increases, and wherein the deformable thrust bearing is configured to increase the pocket depth as the speed of the impeller decreases.

* * * * *